United States Patent [19]

Stoffel

[11] Patent Number: 5,770,390
[45] Date of Patent: Jun. 23, 1998

[54] LIPOHAPTENS COMPRISING A MULTIFUNCTIONAL SUBSTITUTED LIPOHILIC CARRIER LINKED TO AN ANTIGEN AND THEIR USE

[75] Inventor: Wilhelm Stoffel, Cologne, Germany

[73] Assignee: Dade International Inc., Deerfield, Ill.

[21] Appl. No.: 621,050

[22] Filed: Mar. 22, 1996

Related U.S. Application Data

[63] Continuation of Ser. No. 382,837, Feb. 3, 1995, abandoned, which is a continuation of Ser. No. 117,750, Sep. 7, 1993, abandoned, which is a continuation of Ser. No. 879,073, Aug. 1, 1992, abandoned, which is a continuation of Ser. No. 452,098, Dec. 14, 1989, abandoned.

[30] Foreign Application Priority Data

Dec. 22, 1988 [EP] European Pat. Off. .............. 88121536

[51] Int. Cl.$^6$ ................................................. G01N 33/545
[52] U.S. Cl. ........................ 435/7.95; 435/7.94; 436/518; 436/822
[58] Field of Search .................................. 435/7.92, 7.94, 435/7.95; 436/518, 548, 822; 530/350, 359, 403, 405, 406

[56] References Cited

U.S. PATENT DOCUMENTS

| | | | |
|---|---|---|---|
| 4,167,641 | 9/1979 | Welebir . | |
| 4,918,163 | 4/1990 | Young et al. | 424/85.8 |
| 4,965,068 | 10/1990 | Stephan et al. | 530/387 |

FOREIGN PATENT DOCUMENTS

| | | |
|---|---|---|
| 0 256 551 A2 | 2/1988 | European Pat. Off. . |
| 0 066 203 | 7/1981 | United Kingdom . |

OTHER PUBLICATIONS

Synthesis of the Mitogenic S–[2,3–Bis(palmitoyloxy)propyl]–N–palmitoylpentapeptide from *Escherichia coli* Lipoprotein, Weismuller, *Hoppe–Seyler's Z. Physiol. Chem.*, Bd. 364, S. 593–606, May 1983.

A specific immunological probe for the major myelin proteolipid, Confirmation of a deletion in DM–20, Trifileiff, et al., *FEBS* 3489, 198:235–239, Mar. 1986.

Hepatocarcinogenicity of the Trimethyl Homologs of 4–Dimethylaminazobenzene, Brown, et al., *Jour. of Med. Chem.*, 15:212–214, 1972.

1,3(R):4,6(R)–DI–O–Benzyliden–D–Mannit ALS Ausgangsprodukt Für Die Synthese Optisch Aktiver Glycerin–Derivate, Schubert, et al., *Tetrahedron*, 1983.

Preparation of model haptens to express common epitodes of PSP toxins, Guire, et al., *Chemical Abstracts* No. 23, 111:151, 4 Dec. 89–1988/111:210347e.

*Primary Examiner*—Mary E. Ceperley
*Attorney, Agent, or Firm*—Lois K. Ruszala

[57] ABSTRACT

Lipohaptens of the general formula I $$(X)_m\text{—R—Y—}(S)_n\text{—P} \qquad (I)$$

wherein
R is a hydrocarbyl backbone having from 2 to 30 carbon atoms
X is a hydrocarbyl radical having from 6 to 30 carbon atoms, which is linked to R via a bonding group containing one or more heteroatoms
m is an integer from 1 to 5
P is a polypeptide or polysaccharide residue having from 2 to 100 aminoacid or glycosyl units
Y is a functional group capable of binding to a free amino group of the polypeptide P or a carboxy, hemiacetal or hydroxy group of the polysaccharide P
S is a difunctional spacer group, the functional groups thereof being capable of binding with the functional group
Y on the one hand and a free amino, carboxy or hydroxy group of the polypeptide or polysaccaride P on the other hand, and
n is 0 or 1
and their use in immunoreactions for determining antibodies and antigens, respectively.

7 Claims, No Drawings

LIPOHAPTENS COMPRISING A MULTIFUNCTIONAL SUBSTITUTED LIPOHILIC CARRIER LINKED TO AN ANTIGEN AND THEIR USE

This application is a continuation of Ser. No. 08/382,837, filed Feb. 3, 1995, now abandoned, which is a continuation of Ser. No. 08/117,750 filed Sep. 7, 1993, now abandoned, which is a continuation of Ser. No. 07/879,073, filed May 1, 1992, now abandoned, which is a continuation of Ser. No. 07/452,098, filed Dec. 14, 1989, now abandoned.

Antigens used in immunological reactions for diagnostic or therapeutic purposes, in particular proteins, have a considerable molecular size corresponding to a molecular weight of at least 10,000, most often over 100,000 or even over 1 million. In view of their size those proteins are not normally produced synthetically but obtained through biological methods. Whereas it is known that proteins of considerable smaller size can have antigenic properties they have not been used in immunological reactions, i.a. for the reason that they are easily lost in those reactions, be it because of their solubility in the reagents used or because of their non-adherence to usual substrates utilized in immunoassays, such as radioimmunoassay (RIA) or enzyme-linked immunosorbent assay (ELISA).

It has now been found that the aforestated disadvantage can be overcome by utilizing a low molecular weight antigen bound to a multifunctional, substituted lipophilic acceptor molecule as carrier for said low molecular weight antigen.

Accordingly, the invention relates to lipohaptens of the general formula I

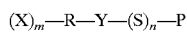

$(X)_m\text{—}R\text{—}Y\text{—}(S)_n\text{—}P$ (I)

wherein
R is a hydrocarbyl backbone having from 2 to 30 carbon atoms
X is a hydrocarbyl radical (and hydrocarbylene radical, respectively) having from 6 to 30 carbon atoms, which is linked to R via a bonding group containing one or more heteroatoms
m is an integer from 1 to 5
P is a polypeptide or polysaccharide residue having from 2 to 100 aminoacid or glycosyl units
Y is a functional group (and said functional group in its reacted form, respectively) capable of binding to a free amino group of the polypeptide P or a carboxy, hemiacetal or hydroxy group of the polysaccharide P
S is a difunctional spacer group, the functional groups thereof being capable of binding with the functional group Y on the one hand and a free amino, carboxy or hydroxy group of the polypeptide or polysaccharide P on the other hand, and
n is 0 or 1.

The hydrocarbyl backbone R has from 2 to 30 carbon atoms, preferably from 3 to 18 carbon atoms. The hydrocarbyl radical can be aliphatic including saturated and unsaturated as well as alicyclic radicals. With aromatic radicals, the minimum number of carbon atoms is obviously 6. Most preferably R is an alkyl radical.

The hydrocarbyl radical X linked to the backbone R has from 6 to 30 carbon atoms, preferably from 12 to 20 carbon atoms and most preferably from 16 to 18 carbon atoms. Aromatic and alicyclic substituents are less prefered so that the prefered substituents X are aliphatic including saturated and unsaturated radicals. Most preferably X is an alkyl or alkenyl radical. The radical X may contain atoms other than carbon and hydrogen as long as the hydrophobicity and biological compatibility is not affected.

The bonding group containing one or more hetero atoms linking the substituent X to the backbone R is preferably a group that is cleavable under biological conditions. Suitable examples are ester, ether, amide, urethane and thiourethane groups. Ester and ether groups are preferred.

m is an integer from 1 to 5, preferably 1, 2 or 3 and most preferably 2. If m is greater than 1, one carbon atom of the backbone R cannot contain more than one substituent X. When m is 2 the two substituents X are preferably located at neighboured carbon atoms. The value of 2 for m is preferred for commercial reasons since these compounds are readily available.

P is a polypeptide or polysaccharide residue having from 2 to 100 basic units, i. e. either aminoacid or glycosyl units. It is noteworthy that the number of units can be as low as 2 or, for example, 3 or 4 or 5. On the other hand, the number of units can be as high as 100 or, for example 80 or 70 or 60 or 50. Preferably the amount of units is from 4 to 50, more preferably from 6 to 40 and most preferably from 5 to 20.

Y is a functional group capable of binding the backbone R to the polypeptide or polysaccharide P, either directly or through a spacer S. Suitable examples for functional groups Y are carboxyl, amino, hydroxy, cyanato and isothiocyanato groups. When n is O and P is a peptide, then Y is preferably a carboxy group or a modified carboxy group so as to obtain an easy linkage with the amino group of the polypeptide.

A spacer S is preferably used when the character of the connecting group between Y and P should be changed. For example, by using a spacer the yield of reaction between the carrier and polypeptide or polysaccharide can be most often considerably improved. In addition, if the reactivity of the group Y binding to P should be changed, this can be done by inserting a spacer S. A preferred spacer group (functional groups not shown), has the formula—$(CH_2)_r$—wherein r is an integer from 2 to 16.

The liphohaptens of the invention comprise lipophilic acceptor molecules or carriers of the general formula II

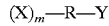

$(X)_m\text{—}R\text{—}Y$ (II)

wherein X, m, R and Y have the aforestated meaning.

A preferred class of carriers of the general formula II are 9,10-dihydroxystearic acid acylated with activated long chain fatty acids to obtain the esters, or alkylated with activated long chain fatty alcohols to yield the respective ethers.

Further preferred classes of carriers are 2,3-diamino-1-propionic acid or 2,3-diamino-1-propanol acylated with activated long chain fatty acids. In the latter case the obtained ester is subjected to alkaline hydrolysis and the free alcoholic groups are then esterified with succinic anhydride.

Yet another preferred class of carriers is obtained by acylation of 2,4-diaminobenzoic acid with activated fatty acids to obtain compounds of the formula

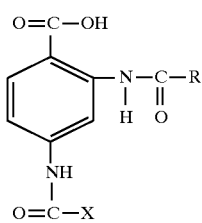

wherein X is a hydrocarbyl residue, preferably alkyl, having from 5 to 25 carbon atoms.

The synthetic antigenic peptides resembling epitopes of the antigen under investigation are synthesized, for example, by the solid phase peptide synthesis of Merrifield or the Fmoc procedure for solid phase peptide synthesis. The linkage of the carrier to the polypeptide is generally effected at the stage of the protected peptide being still linked to the solid phase. The activated lipophilic carrier is then covalently attached to the N-terminus of the peptide. Standard cleavage procedures release the lipophilic carrier covalently linked to the antigenic polypeptide with simultaneous deprotection of amino acid residues, protection of which is demanded during the peptide synthesis. Polysaccharides are coupled to the lipophilic carrier which is extended by a spacer with an $NH_2$-functional group to form a Schiff base with the reducing group of the polysaccharide. This Schiff base may be reduced, for example with sodium borohydride, to convert the imino group to a substituted amino group. In most cases no further purification of the lipohapten comprising the carrier covalently bonded to the polypeptide is required. Otherwise, purification can be effected by various chromatographic methods, such as high performance liquid chromatography or molecular sieve from chromatography. The carriers are introduced as purified compounds in the final coupling step. The antigens are pure because of the solid phase synthesis.

Specific advantages of the lipohaptens of the invention comprising the lipophilic carrier bonded to the antigen, preferably a peptide antigen, reside in that the peptides can be automatically synthesized thus making the system independent on biological production methods. Also, contrary to a known system where an oligopeptide is bonded to a (high molecular) protein, no Freunds adjuvant is necessary which results in uptake by lymphocytes. Finally, in immunological assays, such as RIA or ELISA, the lipohaptens show a good adhesion to the substrate so that there is no danger of losing antigens.

The lipohaptens of the formula I can be used in immunoassays for detecting antibodies and antigens, respectively.

Thus, a further embodiment of the invention relates to a method for the detection of antibodies in a biological liquid, such as a serum or spinal fluid, comprising (a) coating a substrate with a lipohapten of the formula I as defined before carrying an antigen P cognate to said antibodies (b) adding body fluid of a patient to be diagnosed, and (c) detecting the immunological conjugate formed.

Yet another embodiment of the invention relates to a method for detection of antigens in a biological fluid, such as a serum or spinal fluid, comprising (a) coating a substrate with a lipohapten of the formula I as defined before carrying an antibody P cognate to said antigens (b) adding body fluid of a patient to be diagnosed and (c) detecting the immunological conjugate formed.

The detection of said immunological conjugate is achieved by reacting same, for example, with a labeled reagent selected from antihuman immunoglobulin-antibodies and bacterial A protein and detecting the complex formed between said conjugate and said reagent.

Instead of labeling the immunocomplex formed, one can label the antibody and antigen, respectively, before occurance of the immunoreaction.

For commercial purposes, the lipohapten will be in the form of a kit. Accordingly, a further embodiment of the invention resides in a kit for the detection of antibodies in a biological fluid, comprising a lipohapten of the general formula I as defined before, and means for detecting an immunological conjugate formed.

In the aforesaid kit preferred means for detecting said immunological conjugate comprises a reagent selected from antihuman immunoglobulin-antibodies and protein A, and means for detecting the immunological complex formed with said reagent.

A wide variety of immunoassays and modifications thereof, such as direct, indirect, competitive, etc. modifications are available, and the conditions under which such immunoassays are carried out, are likewise well-known. Reference is made to L. Hudson and F. C. Hay "Practical Immunology", 2nd Edition 1980, Handbook of Experimental Immunology, in particular Vol. 1, W. M. Hunter, Radioimmunoassay, Ed. D. M. Weir, 3rd Edition, Chapter 14.2–14.21; Measurement of monoclonal Immunoglobulin concentrations in Hybridoma Cultures by competitive Enzyme Immunoassay, K. W. Hunter & Bosworth, J. M.; Methods in Enzymology, Vol. 121, Chapter 51, pp. 541–547, Ed. Langone, J. J. und van Vunakis, H. 1986; Kemeny, D. M. Challacombe S. J. 1986 "Advances in ELISA and solid phase Immunoassay Immunology today, 7, 67–68, the disclosures of which are incorporated herein by reference. Especially preferred immunoassays for using the lipohaptes of the invention are radioimmunoassay (RIA) and enzyme-linked immunosorbent assay (ELISA).

A procedure for an ELISA test is given below. Water always means distilled water.

1. Costar plates are coated with antigen i.e., the lipohapten of claim 1; concentration 10 µg/ml borate buffered saline

| Di-Na-tetraborate | 0.953 g |
|---|---|
| NaCl | 0.9 g |
| 0.1 N HCl | 17.7 ml |
| Water added to | 100 ml (pH 8.3) |

200 µl per well; 4 hours at room temperature or over night at 4° C.

2. 200 µl 1% BSA (Bovine Serum Albumin) in PBS (Phosphate Buffered Saline); 1–2 hours at room temperature.

3. Wash 2 times with following saline solution.

| NaCl | 8.8 g |
|---|---|
| Tween ™ 20 (1%) | 500 µl |
| NaN₃ | 200 mg |
| add phospate buffer to obtain a final buffer concentration in saline solution of 0.1 M and a final pH of 6.5 | |
| add water to | 1000 ml |

4. Add antiserum, diluted with PBS; 90 minutes at 37° C. or over night at 4° C.

5. Wash 3 times with saline solution.
6. Add 200 µl second antibody coupled with alkaline phosphatase diluted in Trisma buffer 1:1000; 90 minutes at 37° C. or over night at 4° C.

| Trisma buffer | |
| --- | --- |
| BSA | 50 g |
| Tris | 6.05 g |
| $MgCl_2 \times 6\ H_2O$ | 200 mg |
| $NaNa_3$ | 400 mg |
| add water to | 1000 ml (pH 8.0) |

7. Wash 3 times with saline solution.
8. Add 200 µl substrate (30 mg p-nitrophenylphosphate $Na_2$-salt x 5 $H_2O$ in 50 ml buffer.

| Buffer | |
| --- | --- |
| Diethanolamine | 48 ml |
| $MgCl_2 \times 6\ H_2O$ | 24.5 mg |
| add water to | 500 ml (pH 9.8) |

9. Stop reaction with 50 µl N NaOH
10. Measure at 405 nm.

I claim:

1. A method of detection of antibodies in a biological liquid comprising:
   (a) coating a substrate with a lipohapten of the formula $(X)_m$—R—Y—$(S)_n$—P wherein R is a saturated or unsaturated aliphatic or alicyclic hydrocarbyl backbone having from 2 to 30 carbon atoms; X is a saturated or unsaturated aliphatic, aromatic or alicyclic hydrocarbyl radical having from 6 to 30 carbon atoms, which is linked to R via a bonding group consisting of an ester, an ether, an amide, a urethane or a thiourethane; m is an integer from 1 to 5; P is a polypeptide or polysaccharide residue having from 2 to 100 amino acid or glycosyl units; Y is the reacted form of a carboxyl, amino, hydroxy, cyanato or isothiocyanato functional group where, if n=o, Y has bound to a free amino group of the polypeptide P or a carboxyl, hemiacetal or hydroxy group of polysaccharide P or where if n=1 Y has bound to S; S is a difunctional spacer group, the functional groups thereof being capable of binding with the functional group Y on the one hand and a free amino, carboxyl or hydroxy group of the polypeptide or polysaccharide P on the other hand, wherein P is antigenic to said antibodies;
   (b) adding body fluid of a patient to be diagnosed, resulting in the formation of a detectable immunological conjugate; and
   (c) detecting the immunological conjugate formed.

2. A method for the detection of antigens in a biological fluid comprising:
   (a) coating a substrate with a lipohapten of the formula $(X)_m$—R—Y—$(S)_n$—P wherein R is a saturated or unsaturated aliphatic or alicyclic hydrocarbyl backbone having from 2 to 30 carbon atoms; X is a saturated or unsaturated aliphatic, aromatic or alicyclic hydrocarbyl radical having from 6 to 30 carbon atoms, which is linked to R via a bonding group consisting of an ester, an ether, an amide, a urethane or a thiourethane; m is an integer from 1 to 5; P is a polypeptide or polysaccharide residue having from 2 to 100 amino acid or glycosyl units; Y is the reacted form of a carboxyl, amino, hydroxy, cyanato or isothiocyanato functional group where, if n=o, Y has bound to S; S is a difunctional spacer group, the functional groups thereof being capable of binding with the functional group Y on the one hand and a free amino, carboxyl or hydroxy group of the polypeptide or polysaccharide P on the other hand;
   (b) reacting P with antibodies to which P is antigenic;
   (c) adding body fluid of a patient to be diagnosed, resulting in the formation of a detectable immunological conjugate; and
   (d) detecting the immunological conjugate formed.

3. The method of claim 1 or 2, characterized in that said detection is achieved by reacting said immunological conjugate with a labeled reagent selected from anti species immunoglobulin-antibodies wherein the species is of said patient and bacterial A protein and detecting the complex formed between said conjugate and said reagent.

4. The method of claim 1, characterized by being carried out under standard conditions of RIA or ELISA.

5. A kit for the detection of antibodies in a biological fluid, comprising:
   a lipohapten of the formula $(X)_m$—R—Y—$(S)_n$—P wherein R is a saturated or unsaturated aliphatic or alicyclic hydrocarbyl backbone having from 2 to 30 carbon atoms; X is a saturated or unsaturated aliphatic, aromatic or alicyclic hydrocarbyl radical having from 6 to 30 carbon atoms, which is linked to R via a bonding group consisting of an ester, ether, an amide, a urethane or a thiourethane; m is an integer from 1 to 5; P is a polypeptide or polysaccharide residue having from 2 to 100 amino acid or glycosyl units wherein P is antigenic to said antibodies; Y is a carbonyl, amino, hydroxy, cyanato or isothiocyanato functional group capable of binding to a free amino group of the polypeptide P or a carboxyl, hemiacetal or hydroxy group of the polysaccharide P; S is a difunctional spacer group, the functional groups thereof being capable of binding with the functional group Y on the one hand and a free amino, carbonyl or hydroxy group of the polypeptide or polysaccharide P on the other hand, and n is 0 or 1, and means for detecting an immunological conjugate formed.

6. The kit of claim 5, characterized in that said means for detecting said immunological conjugate comprises a reagent selected from antihuman immunoglobulin—antibodies and protein A and means for detecting the immunological complex formed with said reagent.

7. The method of claim 2, characterized by being carried out under standard conditions of RIA or ELISA.

* * * * *